(12) United States Patent
Gordon

(10) Patent No.: US 10,034,997 B2
(45) Date of Patent: Jul. 31, 2018

(54) PAIN HYPERVIGILANCE DESENSITIZATION SYSTEM AND METHOD

(71) Applicant: Alan Gordon, Los Angeles, CA (US)

(72) Inventor: Alan Gordon, Los Angeles, CA (US)

(73) Assignee: Alan Gordon, Los Angeles, CA (US)

( * ) Notice: Subject to any disclaimer, the term of this patent is extended or adjusted under 35 U.S.C. 154(b) by 148 days.

(21) Appl. No.: 15/081,249

(22) Filed: Mar. 25, 2016

(65) Prior Publication Data
US 2016/0279382 A1 Sep. 29, 2016

Related U.S. Application Data

(60) Provisional application No. 62/139,215, filed on Mar. 27, 2015.

(51) Int. Cl.
| | |
|---|---|
| *A61M 21/02* | (2006.01) |
| *A61M 21/00* | (2006.01) |
| *A61B 5/00* | (2006.01) |
| *G06F 19/00* | (2018.01) |
| *G16H 40/63* | (2018.01) |

(52) U.S. Cl.
CPC ........... *A61M 21/00* (2013.01); *A61B 5/4824* (2013.01); *G06F 19/3481* (2013.01); *G16H 40/63* (2018.01); *A61M 2021/0066* (2013.01); *A61M 2205/3368* (2013.01); *A61M 2205/3553* (2013.01); *A61M 2205/3561* (2013.01); *A61M 2205/3584* (2013.01); *A61M 2205/3592* (2013.01); *A61M 2205/505* (2013.01); *A61M 2209/084* (2013.01); *A61M 2230/06* (2013.01); *A61M 2230/10* (2013.01); *A61M 2230/42* (2013.01); *A61M 2230/432* (2013.01); *A61M 2230/50* (2013.01); *A61M 2230/60* (2013.01); *A61M 2230/65* (2013.01)

(58) Field of Classification Search
CPC ......... A61N 7/00; A61N 1/36021; A61F 7/12; A61F 2007/126; A61M 21/02; A61M 2205/505; A61M 2205/3584; A61M 2230/005
USPC ............................ 600/26–28; 128/897, 898
See application file for complete search history.

(56) References Cited

U.S. PATENT DOCUMENTS

| | | | | |
|---|---|---|---|---|
| 4,233,986 | A * | 11/1980 | Tannenbaum | A61N 1/36021 607/46 |
| 8,355,797 | B2 * | 1/2013 | Caparso | A61N 1/025 607/30 |
| 9,241,665 | B2 * | 1/2016 | deCharms | A61B 5/4824 |
| 2016/0038769 | A1 * | 2/2016 | Sullivan | A61N 2/008 601/2 |

\* cited by examiner

*Primary Examiner* — Samuel Gilbert
(74) *Attorney, Agent, or Firm* — Troutman Sanders LLP; Ryan A. Schneider; Christopher C. Close, Jr.

(57) ABSTRACT

In an example embodiment of the disclosed technology, a system can comprise a pain stimulator such as a thermal probe and a device for evaluating biological and/or neurological feedback that can provide data relating to a patient's physiological and/or neurological state. Embodiments of the disclosed technology may further comprise a computing device for implementing various aspects of the technology. Aspects of the disclosed technology can be used to reduce a patient's pain-related anxiety, thus reducing a patient's pain sensitization and pain perception, which can help a patient eliminate or lessen chronic pain symptoms.

1 Claim, 4 Drawing Sheets

PAIN HYPERVIGILANCE DESENSITIZATION SYSTEM AND METHOD

CROSS-REFERENCE TO RELATED APPLICATION

This application claims priority to and benefit under 35 U.S.C § 119(e) of U.S. Provisional Patent Application Ser. No. 62/139,215, entitled "Pain Hypervigilance Desensitization System and Method," filed Mar. 27, 2015, which is hereby incorporated by reference in its entirety as if fully set forth below.

BACKGROUND

Research has shown that pain-related anxiety increases sensitivity to and perception of a particular pain. Research also shows that pain-related anxiety can perpetuate and exacerbate chronic pain symptoms. Accordingly, what is needed is a system and method that utilizes the psychological technique of systematic desensitization to specific pain to reduce pain-related anxiety.

SUMMARY

Some or all of the above needs may be addressed by certain embodiments of the disclosed technology. According to an example embodiment, a method is provided. The method may include providing, via a pain hypervigilance desensitization system ("PHDS"), a pain stimulus to a patient and receiving biofeedback and/or neurofeedback from the patient relating to the patient's response to the pain stimulus. The method may further include determining whether the patient has achieved a sufficient level of calm while experiencing the pain stimulus. The method may further include determining whether the patient has become adept at managing pain at increased pain levels and, if the patient has become so adept, providing a pain stimulus of random intensity and duration.

Other embodiments, features, and aspects of the disclosed technology are described in detail herein and are considered a part of the claimed disclosed technology. The various embodiments, features, and aspects can be understood with reference to the following detailed description, accompanying drawings, and claims.

BRIEF DESCRIPTION OF THE FIGURES

Reference will now be made to the accompanying figures and flow diagrams, which are not necessarily drawn to scale, and wherein.

DETAILED DESCRIPTION

Figure 1:
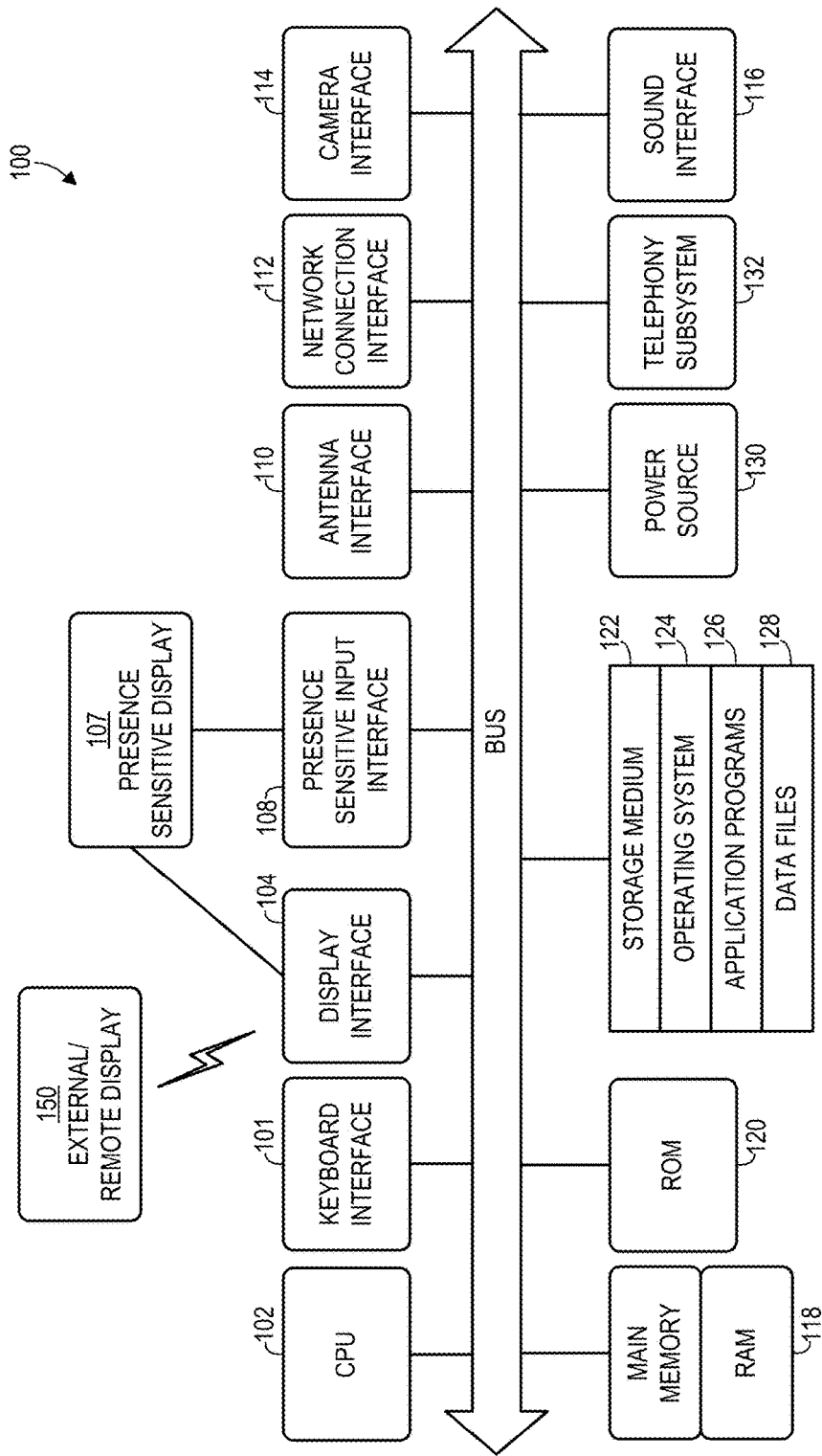
FIG. 1 is a block diagram of an illustrative computer system architecture 100, according to an example embodiment.

In some embodiments, a pain hypervigilance desensitization system ("PHDS") can be utilized to reduce pain-related anxiety, thus reducing pain sensitization and pain perception as well as helping to cease and lessen chronic pain symptoms. In particular, a PHDS can provide a patient with experience regulating anxiety while simultaneously experiencing pain. An exemplary PHDS can comprise a pain stimulator (e.g., a thermal probe) and a device for evaluating biological and/or neurological feedback ("feedback device") that serves to provide data relating to a patient's physiological and/or neurological state. The PHDS can further comprise a computing device.

In some embodiments, a pain stimulator may subject a patient to low-level pain stimulation. The feedback device can detect and provide biological and/or neurological response data ("response data") relating to the patient's response to the pain stimulation. Based on the response data, the PHDS can alter the severity of the pain stimulation. For example, if the response data indicates the patient has achieved a sufficient level of physiological calm (i.e., the patient has become adept at regulating his anxiety while experiencing the low-level pain stimulation), the PHDS may increase the pain stimulation. Accordingly, the patient will grow accustomed to regulating their anxiety while experiencing various predetermined pain stimulation levels. In some embodiments, once the patient becomes adept at managing his pain at the increased levels (i.e., in the later stages of treatment), a PHDS can randomize the intensity and duration of a pain stimulus. As will be understood and appreciated, randomizing the intensity and duration of a pain stimulus can better mimic the uncertainty and unpredictability of organically developing pain, which can allow a patient to learn to develop neural pathways that allow them to more easily reduce their anxiety in response to the onset of pain so that they can do so more successfully when experiencing spontaneously generated pain. Ultimately, by utilizing a PHDS, a patient can increase his ability to regulate anxiety at the onset of pain that can result in a decrease in pain frequency, pain intensity, and pain-related anxiety.

Some embodiments of the disclosed technology will be described more fully hereinafter with reference to the accompanying drawings. This disclosed technology may, however, be embodied in many different forms and should not be construed as limited to the embodiments set forth herein.

In the following description, numerous specific details are set forth. It is to be understood, however, that embodiments of the disclosed technology may be practiced without these specific details. In other instances, well-known methods, structures and techniques have not been shown in detail in order not to obscure an understanding of this description. References to "one embodiment," "an embodiment," "example embodiment," "various embodiments," etc., indicate that the embodiment(s) of the disclosed technology so described may include a particular feature, structure, or characteristic, but not every embodiment necessarily includes the particular feature, structure, or characteristic. Further, repeated use of the phrase "in one embodiment" does not necessarily refer to the same embodiment, although it may.

Throughout the specification and the claims, the following terms take at least the meanings explicitly associated herein, unless the context clearly dictates otherwise. The term "connected" means that one function, feature, structure, or characteristic is directly joined to or in communication with another function, feature, structure, or characteristic. The term "coupled" means that one function, feature, structure, or characteristic is directly or indirectly joined to or in communication with another function, feature, structure, or characteristic. The term "or" is intended to mean an inclusive "or." Further, the terms "a," "an," and "the" are intended to mean one or more unless specified otherwise or clear from the context to be directed to a singular form.

As used herein, unless otherwise specified the use of the ordinal adjectives "first," "second," "third," etc., to describe a common object, merely indicate that different instances of like objects are being referred to, and are not intended to imply that the objects so described must be in a given sequence, either temporally, spatially, in ranking, or in any other manner.

Example embodiments of the disclosed technology will now be described with reference to the accompanying figures.

As desired, embodiments of the disclosed technology may include a computing device with more or less of the components illustrated in FIG. 1. It will be understood that the computing device architecture 100 is provided for example purposes only and does not limit the scope of the various embodiments of the present disclosed systems, methods, and computer-readable mediums.

The computing device architecture 100 of FIG. 1 includes a central processing unit (CPU) 102, where computer instructions are processed; a display interface 104 that acts as a communication interface and provides functions for rendering video, graphics, images, and texts on the display. In certain example embodiments of the disclosed technology, the display interface 104 may be directly connected to a local display, such as a touch-screen display associated with a mobile computing device. In another example embodiment, the display interface 104 may be configured for providing data, images, and other information for an external/remote display that is not necessarily physically connected to the mobile computing device. For example, a desktop monitor may be utilized for mirroring graphics and other information that is presented on a mobile computing device. In certain example embodiments, the display interface 104 may wirelessly communicate, for example, via a Wi-Fi channel or other available network connection interface 112 to the external/remote display.

In an example embodiment, the network connection interface 112 may be configured as a communication interface and may provide functions for rendering video, graphics, images, text, other information, or any combination thereof on the display. In one example, a communication interface may include a serial port, a parallel port, a general purpose input and output (GPIO) port, a game port, a universal serial bus (USB), a micro-USB port, a high definition multimedia (HDMI) port, a video port, an audio port, a Bluetooth port, a near-field communication (NFC) port, another like communication interface, or any combination thereof. In one example, the display interface 104 may be operatively coupled to a local display, such as a touch-screen display associated with a mobile device. In another example, the display interface 104 may be configured to provide video, graphics, images, text, other information, or any combination thereof for an external/remote display that is not necessarily connected to the mobile computing device. In one example, a desktop monitor may be utilized for mirroring or extending graphical information that may be presented on a mobile device. In another example, the display interface 104 may wirelessly communicate, for example, via the network connection interface 112 such as a Wi-Fi transceiver to the external/remote display.

The computing device architecture 100 may include a keyboard interface 106 that provides a communication interface to a keyboard. In one example embodiment, the computing device architecture 100 may include a presence-sensitive display interface 108 for connecting to a presence-sensitive display 107. According to certain example embodiments of the disclosed technology, the presence-sensitive display interface 108 may provide a communication interface to various devices such as a pointing device, a touch screen, a depth camera, etc. which may or may not be associated with a display.

The computing device architecture 100 may be configured to use an input device via one or more of input/output interfaces (for example, the keyboard interface 106, the display interface 104, the presence sensitive display interface 108, network connection interface 112, camera interface 114, sound interface 116, etc.) to allow a user to capture information into the computing device architecture 100. The input device may include a mouse, a trackball, a directional pad, a track pad, a touch-verified track pad, a presence-sensitive track pad, a presence-sensitive display, a scroll wheel, a digital camera, a digital video camera, a web camera, a microphone, a sensor, a smartcard, and the like. Additionally, the input device may be integrated with the computing device architecture 100 or may be a separate device. For example, the input device may be an accelerometer, a magnetometer, a digital camera, a microphone, and an optical sensor.

Example embodiments of the computing device architecture 100 may include an antenna interface 110 that provides a communication interface to an antenna; a network connection interface 112 that provides a communication interface to a network. As mentioned above, the display interface 104 may be in communication with the network connection interface 112, for example, to provide information for display on a remote display that is not directly connected or attached to the system. In certain embodiments, a camera interface 114 is provided that acts as a communication interface and provides functions for capturing digital images from a camera. In certain embodiments, a sound interface 116 is provided as a communication interface for converting sound into electrical signals using a microphone and for converting electrical signals into sound using a speaker. According to example embodiments, a random access memory (RAM) 118 is provided, where computer instructions and data may be stored in a volatile memory device for processing by the CPU 102.

According to an example embodiment, the computing device architecture 100 includes a read-only memory (ROM) 120 where invariant low-level system code or data for basic system functions such as basic input and output (I/O), startup, or reception of keystrokes from a keyboard are stored in a non-volatile memory device. According to an example embodiment, the computing device architecture 100 includes a storage medium 122 or other suitable type of memory (e.g. such as RAM, ROM, programmable read-only memory (PROM), erasable programmable read-only memory (EPROM), electrically erasable programmable read-only memory (EEPROM), magnetic disks, optical disks, floppy disks, hard disks, removable cartridges, flash drives), where the files include an operating system 124, application programs 126 (including, for example, a web browser application, a widget or gadget engine, and or other applications, as necessary) and data files 128 are stored. According to an example embodiment, the computing device architecture 100 includes a power source 130 that provides an appropriate alternating current (AC) or direct current (DC) to power components.

According to an example embodiment, the computing device architecture 100 includes a telephony subsystem 132 that allows the device 100 to transmit and receive sound over a telephone network. The constituent devices and the CPU 102 communicate with each other over a bus 134.

According to an example embodiment, the CPU 102 has appropriate structure to be a computer processor. In one arrangement, the CPU 102 may include more than one processing unit. The RAM 118 interfaces with the computer bus 134 to provide quick RAM storage to the CPU 102 during the execution of software programs such as the operating system application programs, and device drivers. More specifically, the CPU 102 loads computer-executable process steps from the storage medium 122 or other media into a field of the RAM 118 in order to execute software programs. Data may be stored in the RAM 118, where the data may be accessed by the computer CPU 102 during execution. In one example configuration, the device architecture 100 includes at least 128 MB of RAM, and 256 MB of flash memory.

The storage medium 122 itself may include a number of physical drive units, such as a redundant array of independent disks (RAID), a floppy disk drive, a flash memory, a USB flash drive, an external hard disk drive, thumb drive, pen drive, key drive, a High-Density Digital Versatile Disc (HD-DVD) optical disc drive, an internal hard disk drive, a Blu-Ray optical disc drive, or a Holographic Digital Data Storage (HDDS) optical disc drive, an external mini-dual in-line memory module (DIMM) synchronous dynamic random access memory (SDRAM), or an external micro-DIMM SDRAM. Such computer readable storage media allow a computing device to access computer-executable process steps, application programs and the like, stored on removable and non-removable memory media, to off-load data from the device or to upload data onto the device. A computer program product, such as one utilizing a communication system may be tangibly embodied in storage medium 122, which may comprise a machine-readable storage medium.

According to one example embodiment, the term computing device, as used herein, may be a CPU, or conceptualized as a CPU (for example, the CPU 102 of FIG. 1). In this example embodiment, the computing device (CPU) may be coupled, connected, and/or in communication with one or more peripheral devices, such as display. In another example embodiment, the term computing device, as used herein, may refer to a mobile computing device such as a smartphone, tablet computer, or smart watch. In this example embodiment, the computing device may output content to its local display and/or speaker(s). In another example embodiment, the computing device may output content to an external display device (e.g., over Wi-Fi) such as a TV or an external computing system.

In example embodiments of the disclosed technology, a computing device may include any number of hardware and/or software applications that are executed to facilitate any of the operations. In example embodiments, one or more I/O interfaces may facilitate communication between the computing device and one or more input/output devices. For example, a universal serial bus port, a serial port, a disk drive, a CD-ROM drive, and/or one or more user interface devices, such as a display, keyboard, keypad, mouse, control panel, touch screen display, microphone, etc., may facilitate user interaction with the computing device. The one or more I/O interfaces may be utilized to receive or collect data and/or user instructions from a wide variety of input devices. Received data may be processed by one or more computer processors as desired in various embodiments of the disclosed technology and/or stored in one or more memory devices.

One or more network interfaces may facilitate connection of the computing device inputs and outputs to one or more suitable networks and/or connections; for example, the connections that facilitate communication with any number of sensors associated with the system. The one or more network interfaces may further facilitate connection to one or more suitable networks; for example, a local area network, a wide area network, the Internet, a cellular network, a radio frequency network, a Bluetooth enabled network, a Wi-Fi enabled network, a satellite-based network any wired network, any wireless network, etc., for communication with external devices and/or systems.

Figure 2:
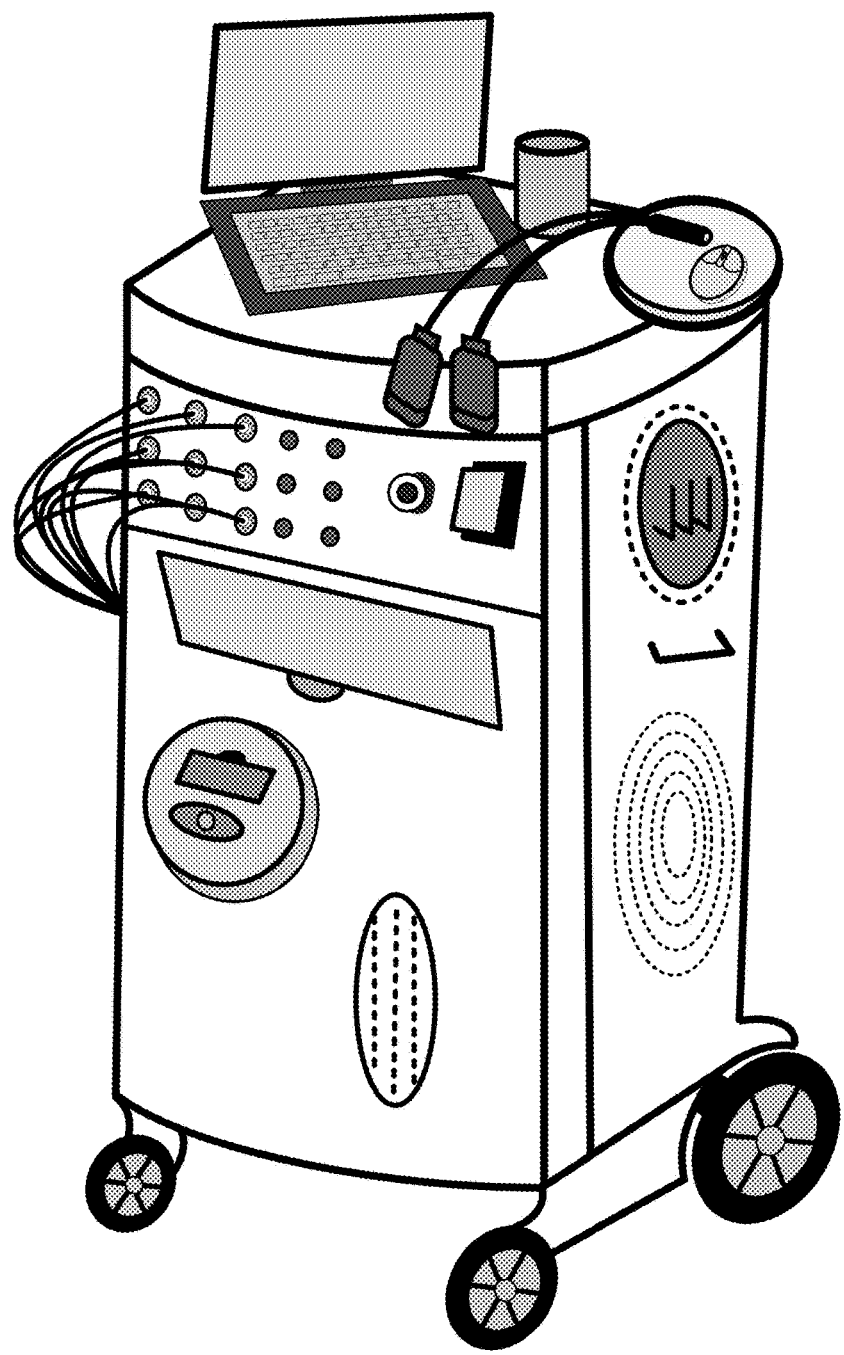
FIG. 2 is an overview of a pain hypervigilance desensitization system ("PHDS") 200, according to an example embodiment.

FIG. 2 illustrates an overview of a pain hypervigilance desensitization system ("PHDS") 200, which may alternatively be referred to as a pain hypervigilance desensitization unit, according to some embodiments. As discussed herein, in some embodiments, a PHDS 200 can comprise some or all of the components of the computer system architecture 100 shown in FIG. 1. Further, in some embodiments, a PHDS 200 may comprise a pain stimulator. For example, in some embodiments, a pain stimulator may comprise one or more thermal probes configured to deliver a heat stimulus to a patient. The thermal probes can be attached to the patient's skin, thus allowing a pain stimulator of a PHDS 200 to deliver a thermal stimulation to the patient. In some embodiments, a pain stimulator can be configured to deliver a thermal stimulation to a patient at predetermined temperatures. Various commercially available pain stimulators are known in the art and contemplated for use in various embodiments of a PHDS 200.

In some embodiments, a PHDS 200 may further comprise a feedback device configured to provide detect, measure, and provide biological and/or neurological response data ("response data") that is indicative of a patient's response to a particular pain stimulation. For example, in some embodiments, a feedback device may be configured to detect and measure various biological functions such as, for example and without limitation, breathing rate, brain activity, heart rate, skin temperature, sweating, muscle spasms, and muscle tension (collectively, "response data"). Feedback devices configured for detecting and measuring various biological functions can include capnometers, electromyographs, electrodermographs, electroencephalographs, feedback thermometers, photopleethysmographs, pneumographs, and other similarly configured devices. As discussed, in some embodiments, a PHDS 200 may be configured to utilize response data acquired by a feedback device to make a determination regarding a patient's level of physiological calm while experiencing a pain stimulus. In some embodiments, upon determining that a patient has obtained an acceptable level of physiological calm, a PHDS 200 may increase the pain stimulus to which the patient is subjected. In some embodiments, upon determining that a patient has obtained an acceptable level of physiological calm, a PHDS 200 may provide the patient with positive reinforcement prior to increasing the patient's pain stimulus.

In some embodiments, a PHDS 200 may be configured to autonomously increase or decrease a pain stimulus in response to response data. So, for example, in some embodiments, upon determining that the patient has achieved an acceptable level of physiological calm (i.e., the patient is adequately handling the pain stimulus), the PHDS 200 can be configured to automatically increase or decrease the pain stimulus to which the patient is subjected as needed. In some embodiments, once the patient becomes adept at managing his pain at increased levels, a PHDS 200 can be configured to randomize the intensity and duration of a pain stimulus.

As will be understood and appreciated, randomizing the intensity and duration of a pain stimulus can better mimic the uncertainty and unpredictability of organically developing pain, thus allowing a patient to learn to develop neural pathways that allow the patient to more easily reduce their anxiety in response to the onset of pain, which can allow the patient to do so more successfully when experiencing spontaneously generated pain.

Figure 3A:
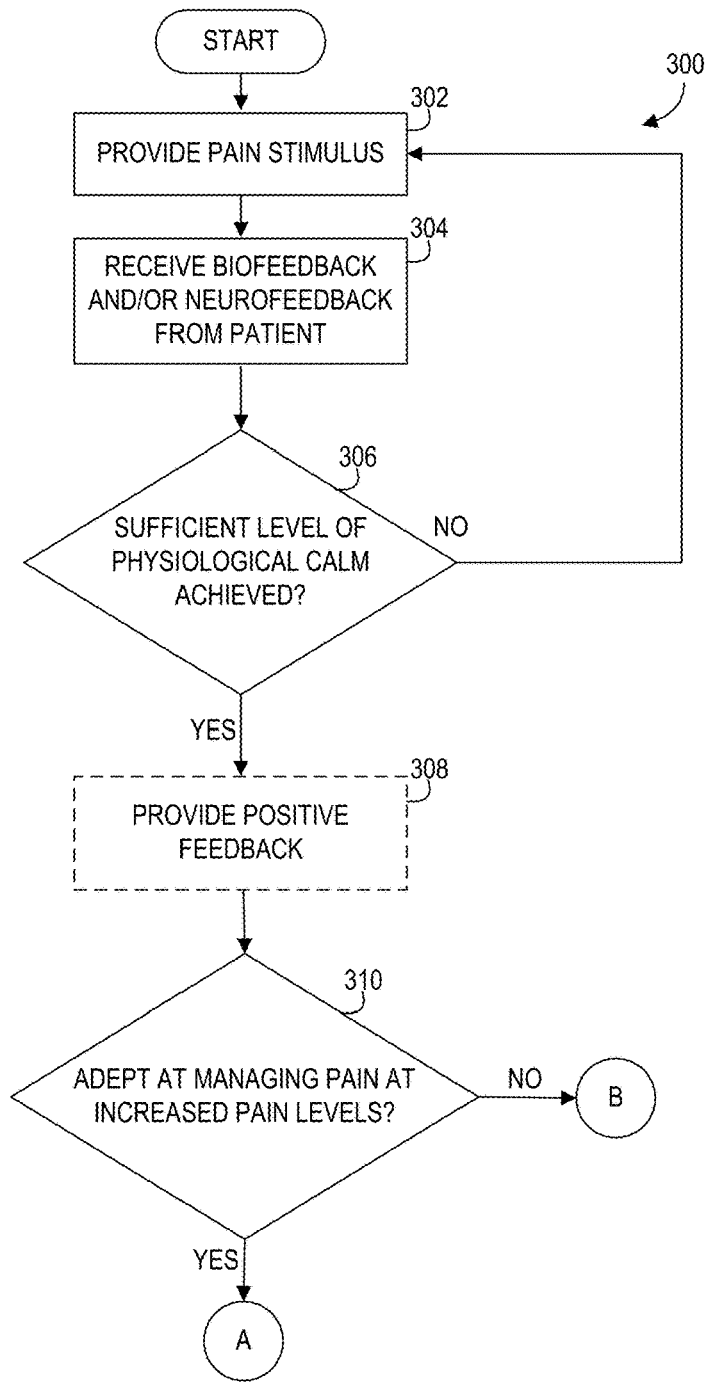
FIGS. 3A-3B are a flow diagram of a method 300 according to an example embodiment.
Figure 3B:
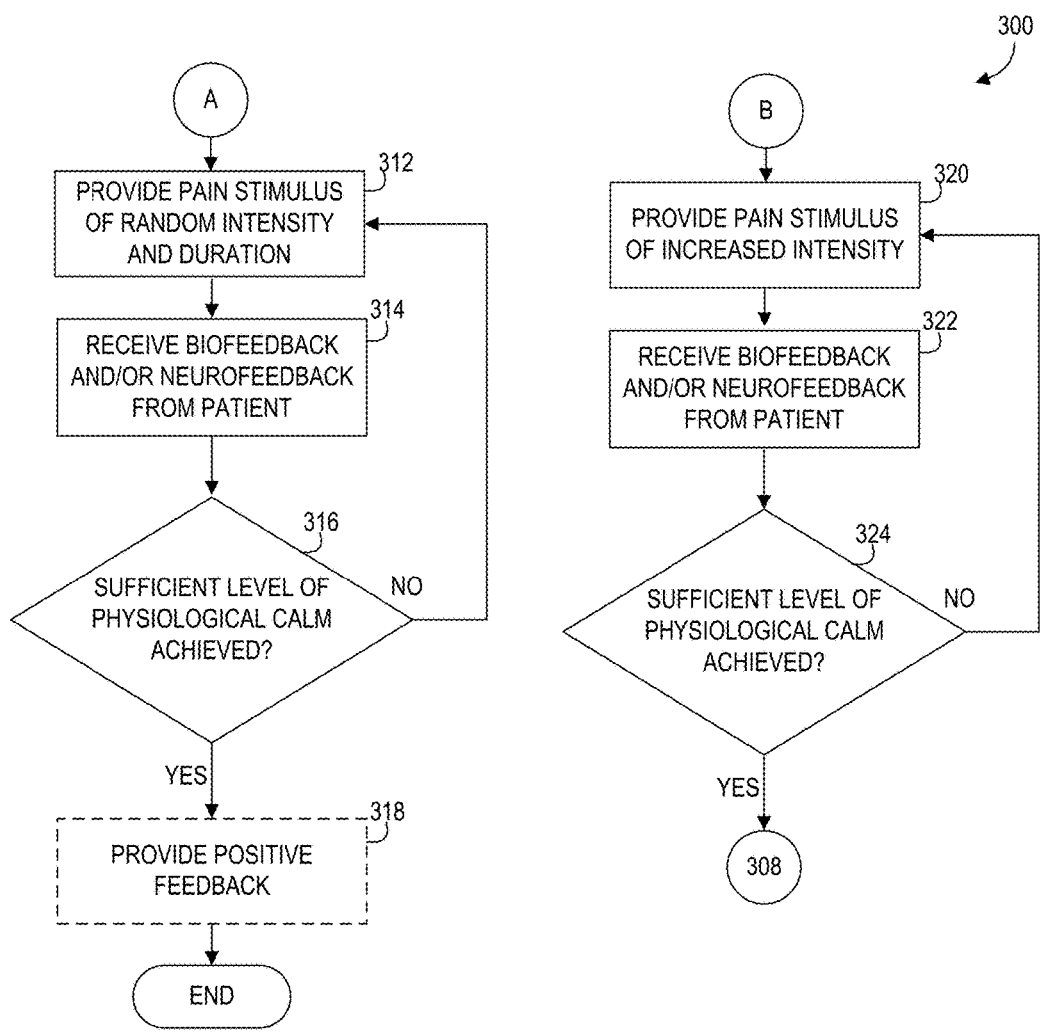

FIGS. 3A-3B are a flow chart illustrating an exemplary method 300 for utilizing a PHDS 200 to enable a patient to develop neural pathways that allow patients to reduce anxiety in response to the onset of pain, thus allowing a patient to better manage pain symptoms. As shown in FIG. 3A, in some embodiments, a PHDS 200 provides a patient with a pain stimulus, at 302. In some embodiments, at 304, a PHDS 200 can receive biofeedback and/or neurofeedback regarding the patient's response to the pain stimulus. Further, in some embodiments, at 306, a PHDS 200 can determine whether the biofeedback and/or neurofeedback indicate that the patient has achieved a sufficient level of physiological calm. As shown in FIG. 3A, if the patient has not yet achieved a sufficient level of physiological calm, the PHDS 200 may continue to provide the pain stimulus, at 302. But if the PHDS 200 determines the patient has achieved a sufficient level of physiological calm, the PHDS 200 may optionally provide positive feedback to the patient, at 308. For example, in some embodiments, the PHDS 200 may provide to the patient encouraging words or pictures.

In some embodiments, a PHDS 200 may determine whether a patient has become adept at managing pain at increased pain levels, at 310. In some embodiments, if a PHDS 200 determines a patient has become adept at managing pain at increased pain levels, as shown in FIG. 3B, a PHDS 200 may provide a pain stimulus of random intensity and duration, at 312. A PHDS 200 may then receive biofeedback and/or neurofeedback from the patient, at 314, and make a determination as to whether the patient has achieved a sufficient level of physiological calm, at 316. In some embodiments, if the PHDS 200 determines the patient has yet to achieve a sufficient level of physiological calm, the PHDS 200 may continue to provide a pain stimulus of random intensity and duration, at 312. But if the PHDS 200 determines the patient has achieved a sufficient level of physiological calm, the PHDS 200 may provide positive feedback to the patient, at 318, at which point the method ends, according to some embodiments.

In some embodiments, if the PHDS 200 determines the patient is not yet adept at managing pain at increased levels, the PHDS 200 may provide a pain stimulus of increased intensity, at 320. The PHDS 200 may then receive biofeedback and/or neurofeedback from the patient relating to the patient's response to the pain stimulus of increased intensity, at 322. In some embodiments, a PHDS 200 may then determine whether the patient has achieved a sufficient level of physiological calm, at 324. Upon determining the patient has not achieved a sufficient level of physiological calm, the PHDS 200 may continue to provide a pain stimulus of increased intensity, at 320. If, however, the PHDS 200 determines the patient has achieved a sufficient level of physiological calm, the method may continue to 308.

Certain embodiments of the disclosed technology are described above with reference to block and flow diagrams of systems and methods and/or computer program products according to example embodiments of the disclosed technology. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, or may not necessarily need to be performed at all, according to some embodiments of the disclosed technology.

Computer-executable program instructions may be loaded onto a general-purpose computer, a special-purpose computer, a processor, or other programmable data processing apparatus to produce a particular machine, such that the instructions that execute on the computer, processor, or other programmable data processing apparatus create means for implementing one or more functions specified in the flow diagram block or blocks. These computer program instructions may also be stored in a computer-readable memory that can direct a computer or other programmable data processing apparatus to function in a particular manner, such that the instructions stored in the computer-readable memory produce an article of manufacture including instruction means that implement one or more functions specified in the flow diagram block or blocks.

Embodiments of the disclosed technology may provide for a computer program product, comprising a computer-usable medium having a computer-readable program code or program instructions embodied therein, said computer-readable program code adapted to be executed to implement one or more functions specified in the flow diagram block or blocks. The computer program instructions may also be loaded onto a computer or other programmable data processing apparatus to cause a series of operational elements or steps to be performed on the computer or other programmable apparatus to produce a computer-implemented process such that the instructions that execute on the computer or other programmable apparatus provide elements or steps for implementing the functions specified in the flow diagram block or blocks.

Accordingly, blocks of the block diagrams and flow diagrams support combinations of means for performing the specified functions, combinations of elements or steps for performing the specified functions and program instruction means for performing the specified functions. It will also be understood that each block of the block diagrams and flow diagrams, and combinations of blocks in the block diagrams and flow diagrams, can be implemented by special-purpose, hardware-based computer systems that perform the specified functions, elements or steps, or combinations of special-purpose hardware and computer instructions.

While certain embodiments of the disclosed technology have been described in connection with what is presently considered to be the most practical and various embodiments, it is to be understood that the disclosed technology is not to be limited to the disclosed embodiments, but on the contrary, is intended to cover various modifications and equivalent arrangements included within the scope of the appended claims. Although specific terms are employed herein, they are used in a generic and descriptive sense only and not for purposes of limitation.

This written description uses examples to disclose certain embodiments of the disclosed technology, including the best mode, and also to enable any person of ordinary skill to practice certain embodiments of the disclosed technology, including making and using any devices or systems and performing any incorporated methods. The patentable scope of certain embodiments of the disclosed technology is defined in the claims, and may include other examples that occur to those of ordinary skill. Such other examples are intended to be within the scope of the claims if they have structural elements that do not differ from the literal language of the claims, or if they include equivalent structural elements with insubstantial differences from the literal language of the claims.

What is claimed is:

1. A method comprising:
   providing, to a patient, a first pain stimulus;
   receiving, from the patient and based at least in part on the first pain stimulus, biofeedback and/or neurofeedback;
   responsive to determining the patient is not adept at managing pain at an increased pain level:
      providing, to the patient, a second pain stimulus, the second pain stimulus being of greater intensity than the first pain stimulus;
      receiving, from the patient and based at least in part on the second pain stimulus, biofeedback and/or neurofeedback; and
      responsive to receiving a first indication that the patient's current level of physiological calm is less than a first predetermined threshold, providing, to the patient, a first indication of positive feedback; and
   responsive to determining the patient is adept at managing pain at an increased pain level:
      providing, to the patient, a random pain stimulus, the random pain stimulus having random intensity and random duration;
      receiving, from the patient and based at least in part on the random pain stimulus, biofeedback and/or neurofeedback; and
      responsive to receiving a second indication that the patient's current level of physiological calm is less than a second predetermined threshold, providing, to the patient, a second indication of positive feedback.

* * * * *